United States Patent
Fercher

Patent Number: 5,877,856
Date of Patent: Mar. 2, 1999

[54] METHODS AND ARRANGEMENT FOR INCREASING CONTRAST IN OPTICAL COHERENCE TOMOGRAPHY BY MEANS OF SCANNING AN OBJECT WITH A DUAL BEAM

[75] Inventor: Adolf Friedrich Fercher, Vienna, Austria

[73] Assignee: Carl Zeiss Jena GmbH, Jena, Germany

[21] Appl. No.: 855,975

[22] Filed: May 14, 1997

[30] Foreign Application Priority Data

May 14, 1996 [AT] Austria ............. 846/96

[51] Int. Cl.⁶ ............................ G01B 9/02

[52] U.S. Cl. .................. 356/345; 356/351; 356/357

[58] Field of Search .................... 356/345, 357, 356/349, 351; 351/212; 382/133

[56] References Cited

PUBLICATIONS

"Optical Coherence Tomography", Huang et al, Science, Nov. 1991, pp. 1178–1181.

*Primary Examiner*—Samuel A. Turner
*Attorney, Agent, or Firm*—McAulay Nissen Goldberg Kiel & Hand, LLP

[57] ABSTRACT

In optical coherence tomography, a sectional image I(x,z) of an object is obtained in that a light beam scans the object along a x-line on the surface, and the depth z from which light of intensity I is reflected is measured by means of a partial-coherence interferometer. In so doing, a strong medium intensity can cover and conceal small differences in adjacent object points. The invention renders small differences in adjacent object points visible in that the object is illuminated by a dual beam which simultaneously illuminates the object at two adjacent points and whose two components are in opposite phase after traversing the arrangement, so that they cancel one another in a homogeneous object structure. On the other hand, if changes are brought about in the two light bundles by means of the reflectance at the object structure, they do not cancel one another, but rather produce an image signal.

7 Claims, 4 Drawing Sheets

METHODS AND ARRANGEMENT FOR INCREASING CONTRAST IN OPTICAL COHERENCE TOMOGRAPHY BY MEANS OF SCANNING AN OBJECT WITH A DUAL BEAM

BACKGROUND OF THE INVENTION

1. Field of the Invention

This invention is directed to the field of medical optical imaging.

2. Description of the Related Art

In optical coherence tomography, a sectional image of an object is obtained in that a light beam scans the object along a line (e.g., along a straight line on the surface). This scanning movement gives (for example) the x-coordinate of the image. In every x-position along this line, the light beam also penetrates into the object. A tomographic interferometer measures the depth z from which light of intensity I is reflected. In this way, a tomographic image I(x,z) of the object is obtained. This imaging process was first described in the article "Optical Coherence Tomography", Huang, D; Swanson, E. A.; Lin, C. P.; Schuman, J. S.; Stinson, W. G.; Chang, W.; Hee, M. R.; Flotte, T.; Gregory, K.; Puliafito, C. A.; Fujimoto, J., Science, volume 254, 1991, pages 1178–1181.

In this method—as in classical reflected-light microscopy—spatially high-frequency modulations of the scattering potential (this corresponds roughly to the complex refractive index) act as image-generating structures. Whereas optical contrasting methods such as phase contrast and interference contrast have been developed in conventional microscopy to improve visibility of tissue structures, suitable methods for coherence tomography have not yet been discovered.

OBJECT AND SUMMARY OF THE INVENTION

Therefore, it is the primary object of the invention to provide methods and devices for improving contrast in images in coherence tomography.

In accordance with the invention, a method and device provide for increasing contrast in coherence tomography imaging by scanning an object with partially coherent light beams and detecting the depth position of the light reflecting locations in the interior of the object by means of partial-coherence interferometry. The interferometer measurement beam scanning the object is a dual beam obtained by beam splitting. The two interferometric partial beams of the beam division to the object and back to the photodetector in the partial beam interferometer have an overall path difference of $\lambda/2$ or an odd-numbered multiple thereof so that the light beams reflected from the two object points with homogeneous object structure undergo destructive interference in the tomography interferometer.

BRIEF DESCRIPTION OF THE FIGURES

FIG. 5b is a view taken along A-A' of FIG. 5a.

Figure 1:
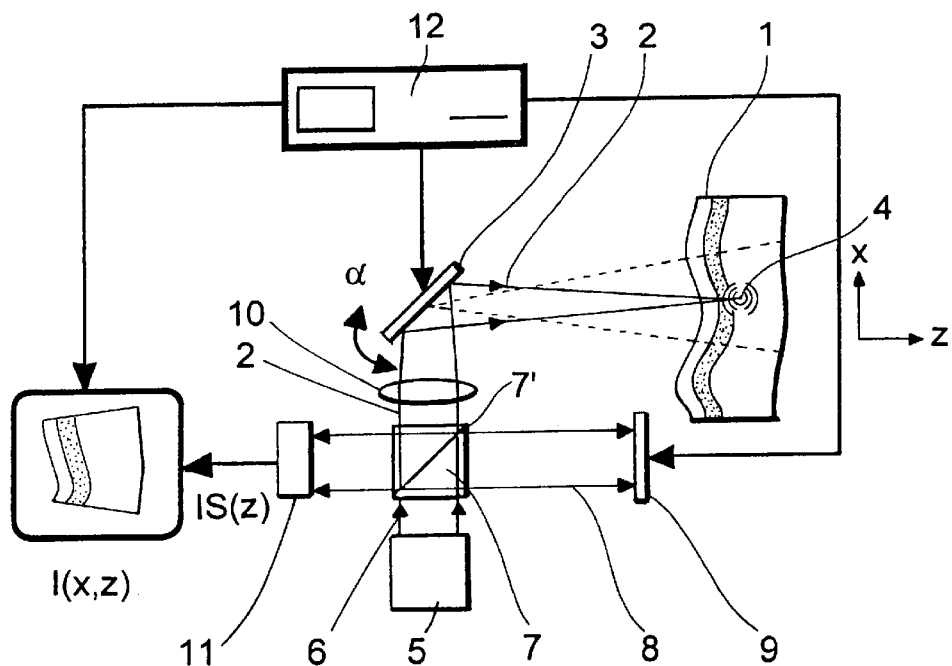
FIG. 1 illustrates the principle of coherence tomography.

1 object
2 measurement light bundle
3 scanning mirror
4 scattering location in object
5 spatially high-coherence and temporally low-coherence light source
6 spatially high-coherence and temporally low-coherence light bundle
7 beam splitter
7' splitter surface of beam splitter 7
8 reference light beam
9 reference light mirror
10 optical system
11 photodetector
12 computer
13 beam splitter deflecting mirror
13' beam splitter surface of beam splitter deflecting mirror 13
13" mirror surface of beam splitter deflecting mirror 13
14' object point or focus of a ray of light in this point
14" object point or focus of a ray of light in this point
15' interferometric partial beam
15" interferometric partial beam
16 optical system
17' interferometric partial beam generated by Wollaston prism
17" interferometric partial beam generated by Wollaston prism
18 Wollaston prism
19 $\lambda/2$ plate
20' compensator plate
20" compensator plate
21 polarizer
22 beam splitter
23 beam splitter end mirror
23' beam splitter surface of 23
23" mirror surface of 23
24 axis
25 beam splitter plate
25' beam splitter surface
26 end mirror
27 fixed base
28 piezoelectric cylinder
29 steel ball

DESCRIPTION OF THE PREFERRED EMBODIMENTS

In the coherence tomography device shown schematically in FIG. 1, the object 1 to be imaged is scanned by a light beam 1. For this purpose, a scanning mirror 3 guides the focussed light beam 2 along a line in the x-direction on the object 1. This line represents one image coordinate, e.g., x, of a two-dimensional image I(x,y). The light beam 2 also penetrates the object 1 and is backscattered with varying degrees of intensity from scattering locations 4 in the interior of the object. The position of these scattering locations 4 forms the second image coordinate designated, for example, as z-coordinate. In coherence tomography, this image coordinate is determined by a tomographic interferometer based on partial-coherence interferometry.

The tomographic partial-coherence interferometer, which is also described briefly with reference to FIG. 1, operates in the following manner: A partially coherent light source 5, e.g., a superluminescent diode, emits a spatially coherent but temporally partially coherent light bundle 6. This light bundle 6 is reflected by the beam splitter 7 partly as interferometric reference light bundle 8 to the reference mirror 9, and transmitted partly as interferometric measurement light beam 2 into the measurement arm of the interferometer. The measurement light bundle 2 is directed to the object 1 by the optical system 10 via the scanning mirror 3. The light reflected from the scattering location 4 is directed back, via the scanning mirror 3 and the optical system 10, to the beam splitter 7 and from there to the photodetector 11. When the optical length in the measurement beam path from the splitter surface 7' to the scattering location 4 within the coherence length is the same as the optical length in the reference beam path from the splitter surface 7' to the deflecting mirror 9, these two light bundles interfere. In order to determine this interference, the reference mirror 9 executes the coherence scan, as it is called; that is, it is moved continuously in the direction of the reference beam. Whenever the length of the reference light beam path is the same as the optical length in the measurement beam path, there is interference between the respective light bundles. In this way, the z-position of the light-reflecting locations in the object is determined. It should be noted that, for the sake of clarity, the length of the reference beam path appears shorter in the following figures than the length of the measurement beam path. The movement of the reference mirror causes the light reflected at this mirror also to undergo a corresponding Doppler shift, and a brightness changing over time is detected by the photodetector 11 as an electric interferometer signal IS(z). For this reason, this method is also referred to as the Doppler method.

The magnitude of the electric interferometer signal IS(z) is proportional to the magnitude of the wave which is backscattered from the object from position z. As was mentioned, the coordinate z is that position of the object for which the optical path lengths in the measurement arm and reference arm are of the same magnitude as calculated from the beam splitter 7. The electric interferometer signal IS is electronically rectified and passed through a bandpass filter; therefore, only signals at Doppler frequency contribute to image formation.

A computer 12 controls the scanning mirror 3 in different positions α which correspond to different x-positions in the object. In each of these positions α, the intensity of the light reflectance along the object depth z is measured by displacing the reference mirror 9. The image I(α,z) or I(x,z) is assembled from these values by means of the same computer or another computer. Thus, a coherence tomography device is formed of two essential units: the scanning unit (in FIG. 1, the scanning mirror 3 with accompanying control) and the partial-coherence interferometer (in FIG. 1, the Michelson interferometer shown with the beam splitter 7 and accompanying control arrangements).

Whereas, in coherence tomography, the object is illuminated only by an individual interferometric measurement light bundle, the object in the method according to the invention is simultaneously illuminated by two partial beams focussed at two points located at a distance from one another, that is, by an "interferometric dual beam". In so doing, the optical path lengths in the device are equalized or adapted in such a way that the light reflected from the two focusses impinges on the photodetector (11) in opposite phase. If amplitude, phase and polarization are affected in the same way in both focusses, the light bundles reflected from the focusses and impinging on the photodetector cancel each other out through destructive interference. In this method, therefore, the only visible structures are those which change over the distance between the two focusses or which have different effects on the amplitude, phase and polarization of the light reflected from the two illuminated points.

Figure 2:
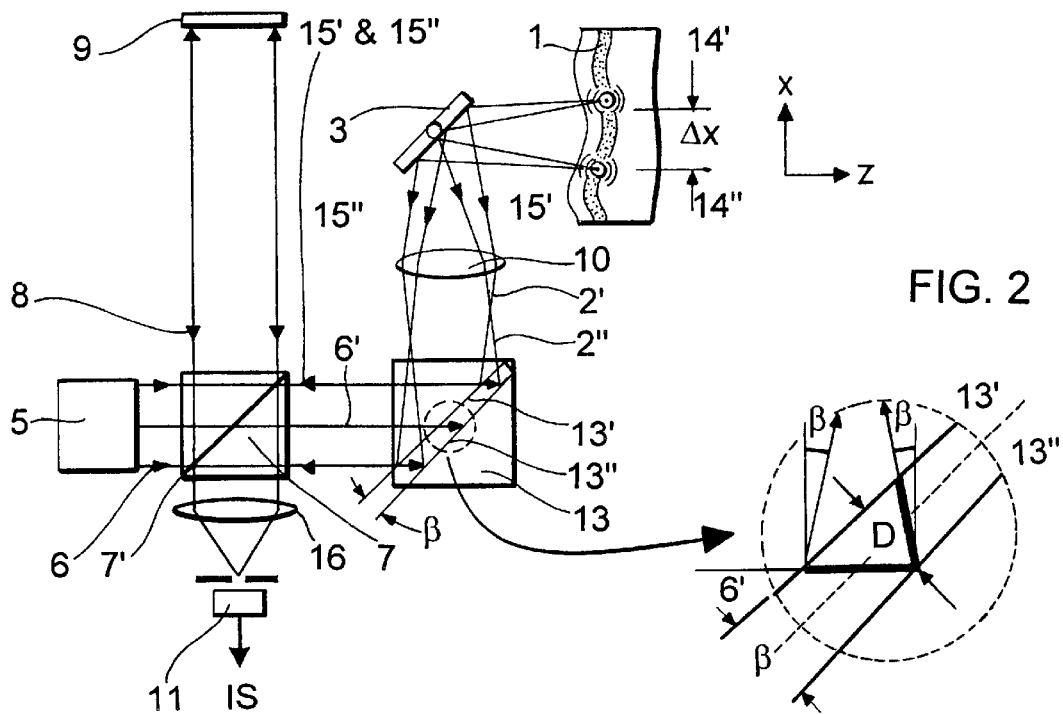
FIG. 2 illustrates a device according to the invention for improving contrast in coherence tomography based on the phases of the reflected light bundles.

In this connection, the focusses of the two partial beams of the dual beam can be spaced in different directions. A device in which this is achieved by a beam splitter deflecting mirror is indicated in FIG. 2. A superluminescent diode 5 emits a spatially coherent but temporally partially coherent light bundle 6. By means of the beam splitter 7, this light bundle 6 is partially reflected to the reference mirror 9 and partially transmitted into the measuring arm of the interferometer. A beam splitter deflecting mirror 13 is located in the measuring arm of the interferometer. The beam splitter deflecting mirror 13 has a beam splitter surface 13' and, behind that, a mirror surface 13". For the destructive interference desired in the present instance, the optical light path from the beam splitter surface 7', via the mirror surface 13" and scanning mirror 3, to the focus 14" and back to the beam splitter surface 7' is greater than the optical light path via 13' to the focus 14' and back by a factor of $(2 \cdot n+1) \cdot \lambda/2$. The symbol n represents the order of interference. Thus, the two light-reflecting surfaces 13' and 13" lie a short distance apart from one another in the propagation direction of the light. Moreover, these two light-reflecting surfaces are inclined relative to one another by an angle β. Because of this wedge angle β, the two light bundles 2' and 2" reflected at surfaces 13' and 13" are focussed in the object 1 by the focussing optical system 10 in two points 14' and 14" which lie at a distance from one another. Owing to the distance between surfaces 13' and 13", the light bundles 2' and 2" undergo a phase shift by an odd-numbered multiple of $\lambda/4$. The two light bundles 15' and 15" reflected in the object from the focusses are collimated by the optical system 10, undergo another phase shift relative to one another by an odd-numbered multiple of $\lambda/4$ at the beam splitter deflecting mirror 13, and finally enter the interferometer again parallel to one another. In the interferometer, the light bundles 15' and 15" are superposed at the splitter surface 7' with the reference light bundle 8 and directed jointly to the photodetector 11 by the optical system 16.

If the two light bundles 15' and 15" have been changed by the object to the same degree with respect to amplitude, phase and polarization or if they remain unchanged, they undergo destructive interference at the photodetector 11, and the electric signal of the photodetector 11 is generated exclusively by the reference light and is constant, which means, e.g., in the Doppler method, that the image signal I(x,z) is zero in this case. However, if these parameters change, for example, because of variation between the object characteristics at points 14' and 14", then there is a resultant light wave from the object 1 which interferes with the reference light 8 and produces a corresponding photodetector signal IS. Thus, differences in the object characteristics of adjacent object points are imaged. In so doing, different reflectance capacities of these points, as well as different phase shifts and different changes in the polarization state in the light reflected from these points result in an interferometer signal IS at the output and accordingly lead to a bright image point. Thus, differences in the object characteristics are imaged on the basis of the spatial difference Δx. The distance Δx between points 14' and 14" is given in the arrangement shown in FIG. 2 by the angle β between surfaces 13' and 13" and focal length $f$ of the optical system 10: $\Delta x = 2 \cdot \beta f$.

The beam splitter deflecting mirror 13 comprises two three-sided partial prisms joined at the hypotenuse faces. Located between the hypotenuse faces is a wedge-shaped gap of air, optical cement or another substance with a reactive index different than that of the prisms and with a wedge angle β. The optical gap thickness Ω (=geometric thickness times refractive index in the gap) in the center of the beam bundle (6') for small angles β and small $$D = \frac{(Z_o n + 1) \cdot \frac{\lambda}{2}}{\frac{4}{\sqrt{2}} \cdot \left[1 + tg\left(\frac{\pi}{4} - \frac{\beta}{2}\right)\right]};$$

tg = goniometric function tar (target)

orders n is expressed by approximation as follows (see FIG. 2):

A device of this kind delivers images which at large values of Δx, correspond to the phase difference method and, at small values of Δx, to the differential interference contrast image of conventional interferometry.

Figure 3:
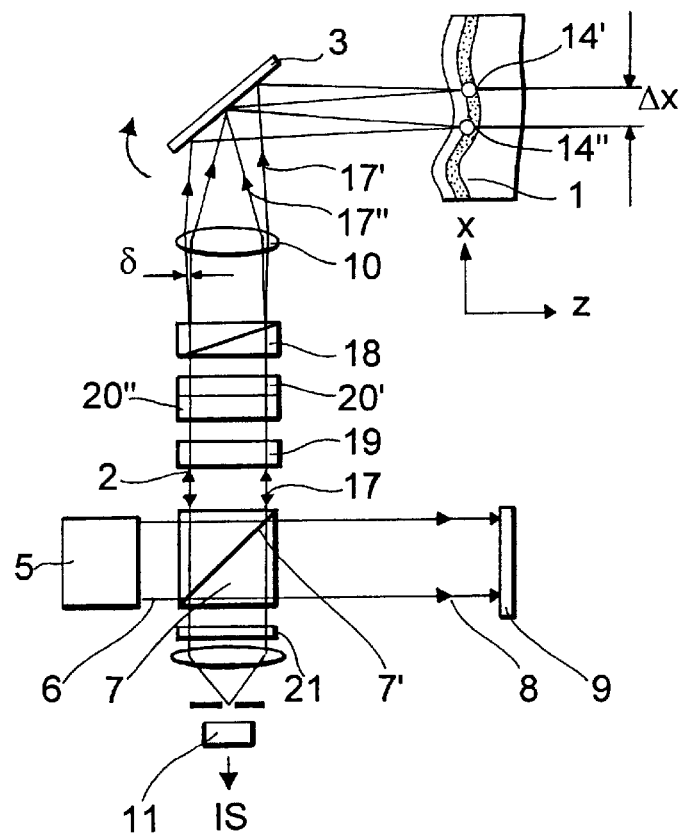
FIG. 3 illustrates a device according to the invention for improving contrast in coherence tomography based on polarization.

FIG. 3 shows an alternative arrangement for optical contrasting according to the method according to the invention. In this case, the object 1 is illuminated by a dual beam with partial beams 17' and 17". This dual beam is formed from the partially coherent light bundle 2 by means of a Wollaston prism 18. The Wollaston prism 18 is formed of two three-sided partial prisms of birefringent material which are joined at the hypotenuse faces. It supplies two linearly polarized waves 17' and 17" vertical to one another which diverge to various degrees depending upon prism geometry and material. For example, when partial prisms with isosceles bases are used, a divergence angle δ of 1° is obtained when quartz crystal is used as material and a divergence angle of 20° is obtained when calcite is used. If the light bundle 6 coming from light source 5 is already polarized, the orientation of the polarization plane of the wave 2 and accordingly the intensities of the partial waves 17' and 17" occurring at the Wollaston prism can be adjusted by means of the λ/2 plate 19. Otherwise, a polarizer is arranged in place of the λ/2 plate 19 and the intensities of the partial waves 17' and 17" can be adjusted via the azimuthal orientation of the polarizer.

In order to compensate for the large optical path difference caused by the birefringent components of the Wollaston prism, it may be necessary to arrange a compensator in the measurement beam path. This compensator is formed of two uniaxial plates 20' and 20" which are rotated by 90° relative to one another so that the slow axis of one plate lies parallel to the fast axis of the second plate. With an appropriate choice of the thickness of the two plates 20' and 20", an overall path difference of λ/2, or an odd-numbered multiple thereof, can be achieved in the measurement beam path for the back-and-forth traveling of the waves from the beam splitter surface 7' to the points 14' and 14" and back to the beam splitter surface 7'. The use of λ/2 plates and compensators is known from the prior art in polarization optics.

Finally, a polarizer 21 is located in the common beam path of the measurement light and reference light in front of the photodetector 11, this polarizer 21 being oriented in such a way that it passes roughly 50% of the intensities of the light bundles coming back from the points 14' and 14" and provides for interference of the passed light components.

In the arrangements according to FIGS. 2 and 3, differences in the object characteristics are imaged based on the spatial difference Δx. Focusses 14' and 14" can also be situated in different z-positions if the Wollaston prism in FIG. 3 is replaced by a birefringent lens. A birefringent lens comprises, for example, a uniaxial birefringent material with the optical axis in the lens plane. A lens of this kind has two different refractive powers for two different polarizing directions which, jointly with the optical system 10, generate two focusses on the optical axis at different depths in the object. Differences in the object structure occurring in the z-direction are then imaged by coherence tomography.

Figure 4:
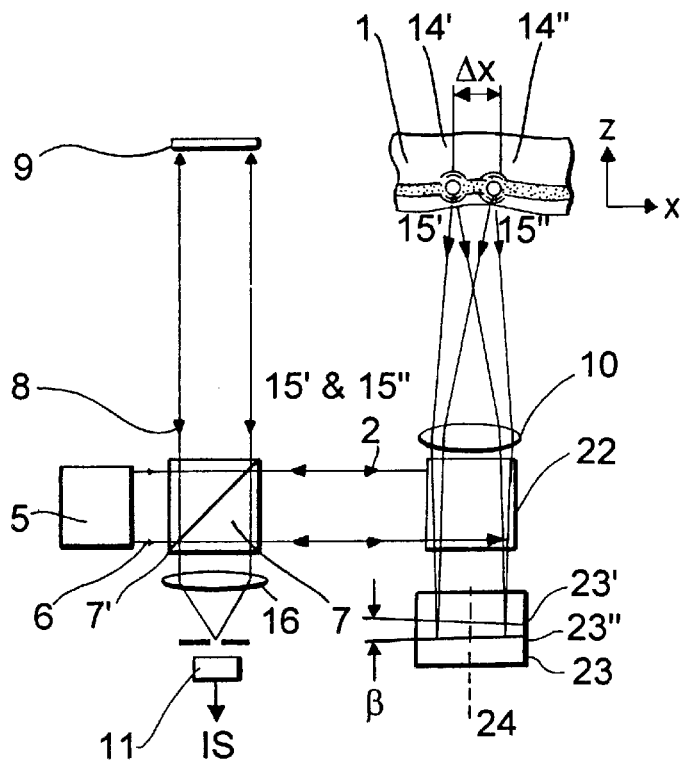
FIG. 4 illustrates a device according to the invention for improving contrast in coherence tomography with azimuthal adjustability of spatial difference.

Rotating the Wollaston prism in the beam path in FIG. 3 about an axis parallel to the axis of the beam 2 changes the orientation of the beam division and accordingly the position of the two focusses 14' and 14" lying at a distance from one another in the x-direction. In order to obtain this degree of freedom in the arrangement with the beam splitter deflecting mirror, as well, the latter must be modified and used in reflection as is shown in FIG. 4. In this case, the measurement light bundle 2 first impinges on the beam splitter 22 and is then deflected to the beam splitter end mirror 23. The latter has a beam splitter surface 23' and a mirror surface 23". These two light-reflecting surfaces lie at an optical distance of λ/8 (or an odd-numbered multiple thereof) from one another in the propagation direction of the light. The light bundles reflected at the beam splitter end mirror 23 are focussed by the optical system 10 in two object points 14' and 14". The light bundles 15' and 15" reflected from these points travel back over the beam splitter end mirror 23 and the beam splitter 22 to the interferometer and are superposed with the reference light bundle 8. The beam splitter end mirror 23 can be arranged so as to be rotatable about an axis 24. The orientation of the two scanning points 14' and 14" in the object can accordingly be optionally adjusted in the x-y plane.

The two light-reflecting surfaces 23' and 23" in the beam splitter end mirror can also be configured in another way. For example, the surface 23' can be oriented normal to the axis and the surface 23" can be formed as a spherical surface. Two focusses which are spaced apart in depth (z-direction) are then obtained in the object and an imaging method is achieved which emphasizes depth differences in the object.

Figure 5A:
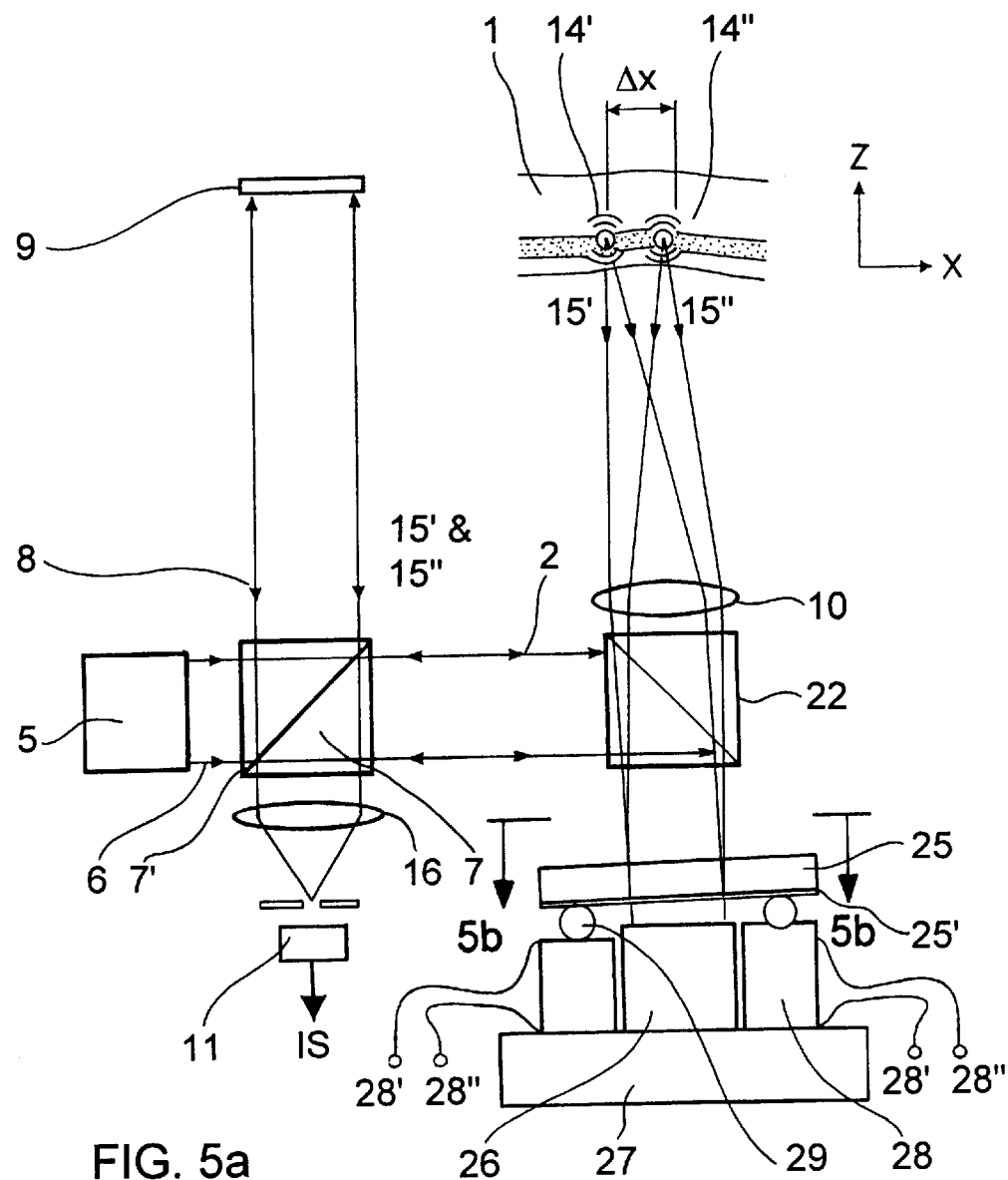
FIG. 5a illustrates a device according to the invention for improving contrast in coherence tomography with continuously adjustable spatial difference.
Figure 5B:
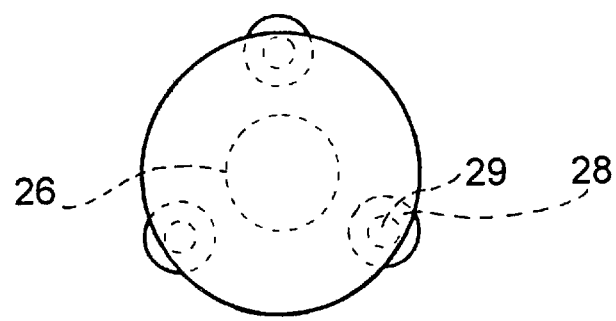

Finally, another embodiment of the method according to the invention in which the spatial difference of the two focusses in the object can be continuously adjusted is shown in FIG. 5. The measurement light bundle 2 is first deflected by the beam splitter 22 onto a piezoelectrically adjustable beam splitter end mirror. The latter is formed of a beam splitter plate 25 with a semitransparent surface 25' and an end mirror 26. The end mirror 26 is firmly seated on a base 27. The beam splitter plate 25 sits on three piezoelectric columns 28 whose length can be regulated by applying a voltage to the connections 28' and 28" (this belongs to the prior art). To prevent mechanical stresses, a steel ball 29 lies between the beam splitter plate 25 and the piezoelectric columns 28. By applying different voltages to the three piezoelectric columns, both the magnitude Δx of the spatial difference for the image contrast as well as the orientation of the spatial difference can be continuously adjusted.

Figure 6:
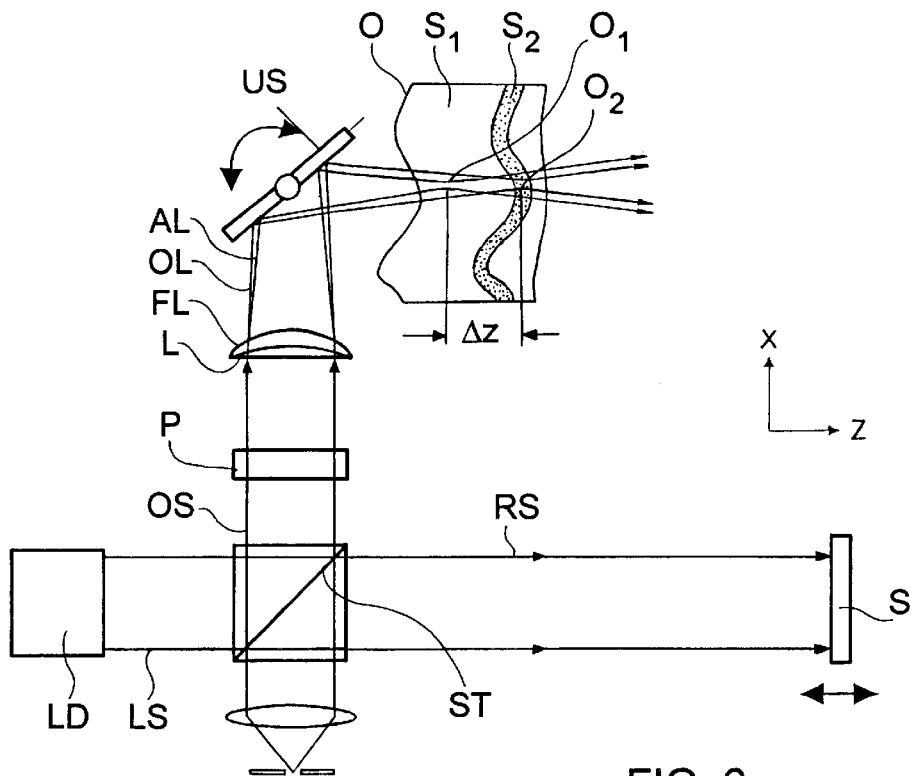
FIGS. 6 and 7 illustrate other variations of the invention. The following reference numbers are used.

In FIG. 6, the superluminescent diode LD emits a temporally short-coherence but spatially fully coherent light beam LS. The beam splitter ST splits the beam into a reference beam RS reflected at the reference mirror S and an object beam OS.

The polarizer P generates linearly polarized light, e.g., at 45° to the optical axis of the birefringent lens L following it. The plano-convex birefringent lens L is produced from quartz or calcite or from another birefringent material. Its optical axis runs parallel to the plane surface. This lens accordingly has two different refractive indices and thus two different focal widths for the ordinary light bundle OL and the extraordinary light bundle AL.

The focussing lens FL additionally focusses the two light bundles OL and AL coming from the birefringent lens L. These light bundles are directed from the deflecting mirror US to the object O. The object comprises structures S1 and S2 which control light in a polarization-dependent manner.

The reference mirror S, for example, is now continuously displaced in OCT A-scan. If there exists within the coherence length of the used light an identity of optical paths from the beam splitter to a light-emitting location in the object and from the beam splitter to the reference mirror S, interference occurs at the interferometer output and is used as an OCT signal to obtain a tomogram.

Now, due to the birefringent lens, there exists an optical path identity simultaneously for two locations lying at a distance from one another along the object depth (z-direction), e.g., 01, 02 in object O. These locations lie apart from one another in the z-direction by an optical distance $\Delta z = d \cdot \Delta n$, where $\Delta n$ is the difference in refractive index of the lens material for the two polarization directions and d is the thickness of the birefringent lens L.

The lens thickness d can be so dimensioned that destructive interference occurs for the reflected light. This is the case for $2 \cdot d \cdot \Delta n =$ odd-numbered multiple of $\lambda$. There is an OCT signal only if the two locations 01 and 02 reflect back light of different intensities (and/or if the scatter light phase is different at these two locations). Thus, an OCT image is obtained which images polarization-dependent scatter differences in two points at a distance $\Delta z$ from one another: *"Differential Polarization Contrast"*.

Figure 7:
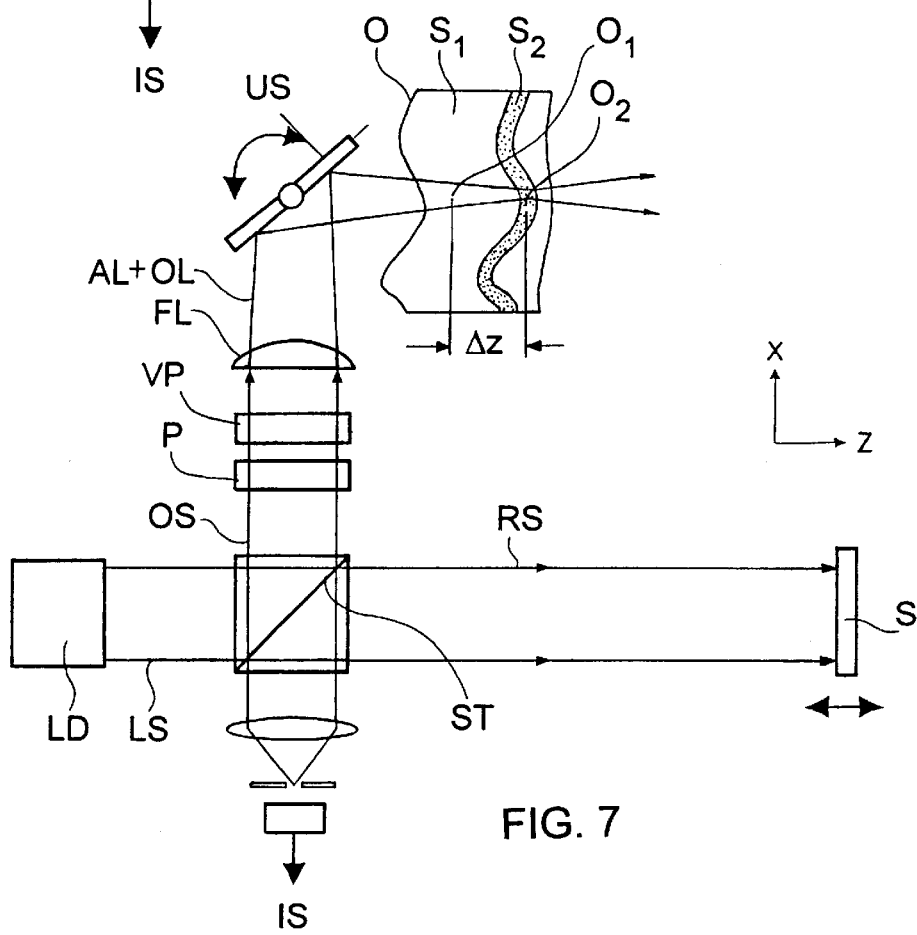

This can also be accomplished without a birefringent lens as is shown in FIG. 7. If the birefringent lens L is omitted and a retarder plate, e.g., a $\lambda/4$ plate (zero order), is arranged between the polarizer P and focussing lens FL, the light undergoes an overall phase shift of $\pi$ when traveling back and forth, i.e., the two light bundles are in opposite phase. Destructive interference occurs between them after polarizer P. Polarization contrast is now obtained for $\Delta z \sim 0$. When a higher-order $\lambda/4$ plate is used, e.g., a plate of thickness D, where $D \cdot \Delta n = (2 \cdot m - 1) \cdot \lambda/2$, and the order number is greater than 1, a polarization contrast is obtained for points lying apart by the optical distance $\Delta z = D \cdot \Delta n$: *Differential Polarization contrast*.

If D and accordingly the order number and $\Delta z$ are very small, this is a case of *"differential polarization contrast"*. Naturally, retarder plates of this kind can also be realized from two plates of unequal thickness which are rotated at 90° relative to one another—as is conventional in polarization technique to avoid excessively thin plates.

While the foregoing description and drawings represent the preferred embodiments of the present invention, it will be obvious to those skilled in the art that various changes and modifications may be made therein without departing from the true spirit and scope of the present invention.

What is claimed is:

1. In a method for increasing contrast in coherence tomography imaging by scanning an object with a partially coherent light beam and detecting the depth position of the light-reflecting locations in the interior of the object by means of partial-coherence interferometry, an improvement comprising the steps of beam splitting the light beam to produce a dual beam, scanning two object points of the object with the dual beam, and detecting two interferometric partial beams to the object and back to a photodetector in a partial-coherence interferometer having an overall path difference of $\lambda/2$ or an odd-numbered multiple thereof, so that light beams reflected from the two object points with homogeneous object structure undergo destructive interference in a tomography interferometer.

2. A device for increasing contrast in coherence tomography imaging according to a method for increasing contrast in coherence tomography imaging by scanning an object with partially coherent light beams and detecting the depth position of the light reflecting locations in the interior of the object by partial-coherence interferometry, said device comprising:

means for obtaining an interferometer measurement beam for scanning the object by beam splitting to create a dual beam having two interferometric partial beams; said two interferometric partial beams having a path length to the object and back to a photodetector in a partial-coherence interferometer having an overall path difference of $\lambda/2$ or an odd-numbered multiple thereof, so that light beams reflected from two object points with homogeneous object structure undergo destructive interference in a tomography interferometer, and wherein the two interferometric partial beams illuminating the object are produced by wavefront division by means of a beam splitter deflecting mirror which has a beam splitter surface and a mirror surface which are inclined at an angle to one another and lie at a distance from one another such that the light path for the two interferometric partial beams during a second passage differs by $\lambda/2$ or an odd-numbered multiple thereof.

3. A device for increasing contrast in coherence tomography imaging according to a method for increasing contrast in coherence tomography imaging by scanning an object with partially coherent light beams and detecting the depth position of the light reflecting locations in the interior of the object by partial-coherence interferometry, said device comprising:

means for obtaining an interferometer measurement beam for scanning the object by beam splitting to create a dual beam having two interferometric partial beams; said two interferometric partial beams having a path length to the object and back to a photodetector in a partial-coherence interferometer having an overall path difference of $\lambda/2$ or an odd-numbered multiple thereof, so that light beams reflected from two object points with homogeneous object structure undergo destructive interference in a tomography interferometer, and wherein the two interferometric partial beams illuminating the object are produced by wavefront division by means of a beam splitter end mirror which is rotatable about an axis and has a beam splitter surface and a mirror surface which are inclined at an angle relative to one another and lie at a distance from one another such that the light path for the two interferometric partial beams during a second passage differs by $\lambda/2$ or an odd-numbered multiple thereof.

4. A device for increasing contrast in coherence tomography imaging according to a method for increasing contrast in coherence tomography imaging by scanning an object with partially coherent light beams and detecting the depth position of the light reflecting locations in the interior of the object by partial-coherence interferometry, said device comprising:

means for obtaining an interferometer measurement beam for scanning the object by beam splitting to create a dual beam having two interferometric partial beams; said two interferometric partial beams having a path length to the object and back to a photodetector in a partial-coherence interferometer having an overall path difference of $\lambda/2$ or an odd-numbered multiple thereof, so that light beams reflected from two object points with homogeneous object structure undergo destructive interference in a tomography interferometer, and wherein the two interferometric partial beams illuminating the object are produced by wavefront division by means of a Wollaston prism and a path difference for these two partial beams is adjusted by means of a compensator to $\lambda/2$ or an odd-numbered multiple thereof.

5. A device for increasing contrast in coherence tomography imaging according to a method for increasing contrast in coherence tomography imaging by scanning an object with partially coherent light beams and detecting the depth position of the light reflecting locations in the interior of the object by partial-coherence interferometry, said device comprising:

means for obtaining an interferometer measurement beam for scanning the object by beam splitting to create a dual beam having two interferometric partial beams; said two interferometric partial beams having a path length to the object and back to a photodetector in a partial-coherence interferometer having an overall path difference of $\lambda/2$ or an odd-numbered multiple thereof, so that light beams reflected from two object points with homogeneous object structure undergo destructive interference in a tomography interferometer, and wherein the two interferometric partial beams illuminating the object are produced by wavefront division by means of a birefringent lens and a path difference for these two partial beams is adjusted by means of a compensator to $\lambda/2$ or an odd-numbered multiple thereof.

6. A device for increasing contrast in coherence tomography imaging according to a method for increasing contrast in coherence tomography imaging by scanning an object with partially coherent light beams and detecting the depth position of the light reflecting locations in the interior of the object by partial-coherence interferometry, said device comprising:

means for obtaining an interferometer measurement beam for scanning the object by beam splitting to create a dual beam having two interferometric partial beams; said two interferometric partial beams having a path length to the object and back to a photodetector in a partial-coherence interferometer having an overall path difference of $\lambda/2$ or an odd-numbered multiple thereof, so that light beams reflected from two object points with homogeneous object structure undergo destructive interference in a tomography interferometer, and wherein the two interferometric partial beams illuminating the object are produced by wavefront division by means of a piezoelectrically controlled beam splitter end mirror having a beam splitter surface and a mirror surface which can be adjusted at an angle and at a distance relative to one another by piezoelectric columns in such a way that the light path for the two interferometric partial beams during a second passage differs by $\lambda/2$ or an odd-numbered multiple thereof.

7. A device for increasing contrast in coherence tomography imaging according to a method for increasing contrast in coherence tomography imaging by scanning an object with partially coherent light beams and detecting the depth position of the light reflecting locations in the interior of the object by partial-coherence interferometry, said device comprising:

means for obtaining an interferometer measurement beam for scanning the object by beam splitting to create a dual beam having two interferometric partial beams; said two interferometric partial beams having a path length to the object and back to a photodetector in a partial-coherence interferometer having an overall path difference of $\lambda/2$ or an odd-numbered multiple thereof, so that light beams reflected from two object points with homogeneous object structure undergo destructive interference in a tomography interferometer, and wherein a phase shift of beams illuminating the object is produced by optical polarizing means.

* * * * *